(12) United States Patent
Pratt

(10) Patent No.: US 6,669,255 B2
(45) Date of Patent: Dec. 30, 2003

(54) APPARATUS FOR INHIBITING CONTAMINATION OF SAMPLE DURING BAILER EMPTYING

(76) Inventor: David W. Pratt, 13512 Feather Sound Cir. West, Apt. 1401, Clearwater, FL (US) 33762

( * ) Notice: Subject to any disclaimer, the term of this patent is extended or adjusted under 35 U.S.C. 154(b) by 72 days.

(21) Appl. No.: 09/683,904

(22) Filed: Feb. 28, 2002

(65) Prior Publication Data

US 2003/0160469 A1 Aug. 28, 2003

(51) Int. Cl.[7] .................. F16K 15/06; F16K 15/04; G01N 1/12
(52) U.S. Cl. ................ 294/68.25; 73/864.3; 73/864.4; 166/264
(58) Field of Search .............. 294/68.22, 68.25; 166/66, 66.6, 66.7, 99, 264, 332.1–332.3, 162; 73/864.63, 864.64, 864.65, 864.66, 864.67, 863.71, 863; 206/524.8; 383/41

(56) References Cited

U.S. PATENT DOCUMENTS

| | | | | |
|---|---|---|---|---|
| 1,210,487 A | * | 1/1917 | Kaul | 73/864.63 |
| 2,223,936 A | * | 12/1940 | Hart | 294/68.25 |
| 2,298,627 A | * | 10/1942 | Proudman | 73/864.63 |
| 4,050,315 A | * | 9/1977 | Markfelt | 73/864.66 |
| 4,561,315 A | * | 12/1985 | Ontek | 73/864.64 |
| 5,996,800 A | * | 12/1999 | Pratt | 206/524.8 |
| 6,276,220 B1 | * | 8/2001 | Varhol | 73/863.21 |
| 6,543,302 B1 | * | 4/2003 | Pratt | 294/68.22 |

* cited by examiner

Primary Examiner—Eileen D. Lillis
Assistant Examiner—Paul T. Chin
(74) Attorney, Agent, or Firm—Ronald E. Smith; Smith & Hopen, P.A.

(57) ABSTRACT

A bailer collects a column of liquid fluid of predetermined height from a body of liquid fluid at a predetermined depth. The bailer is emptied without contaminating the collected liquid fluid with oxygen. The bailer has two check valves spaced apart from one another by a preselected distance so that it can collect liquid fluid at a predetermined depth below the surface of the body of liquid fluid. A vent opening is formed between the first check valve and the second check valve to enable the bailer to be emptied in the substantial absence of oxygen contamination.

5 Claims, 2 Drawing Sheets

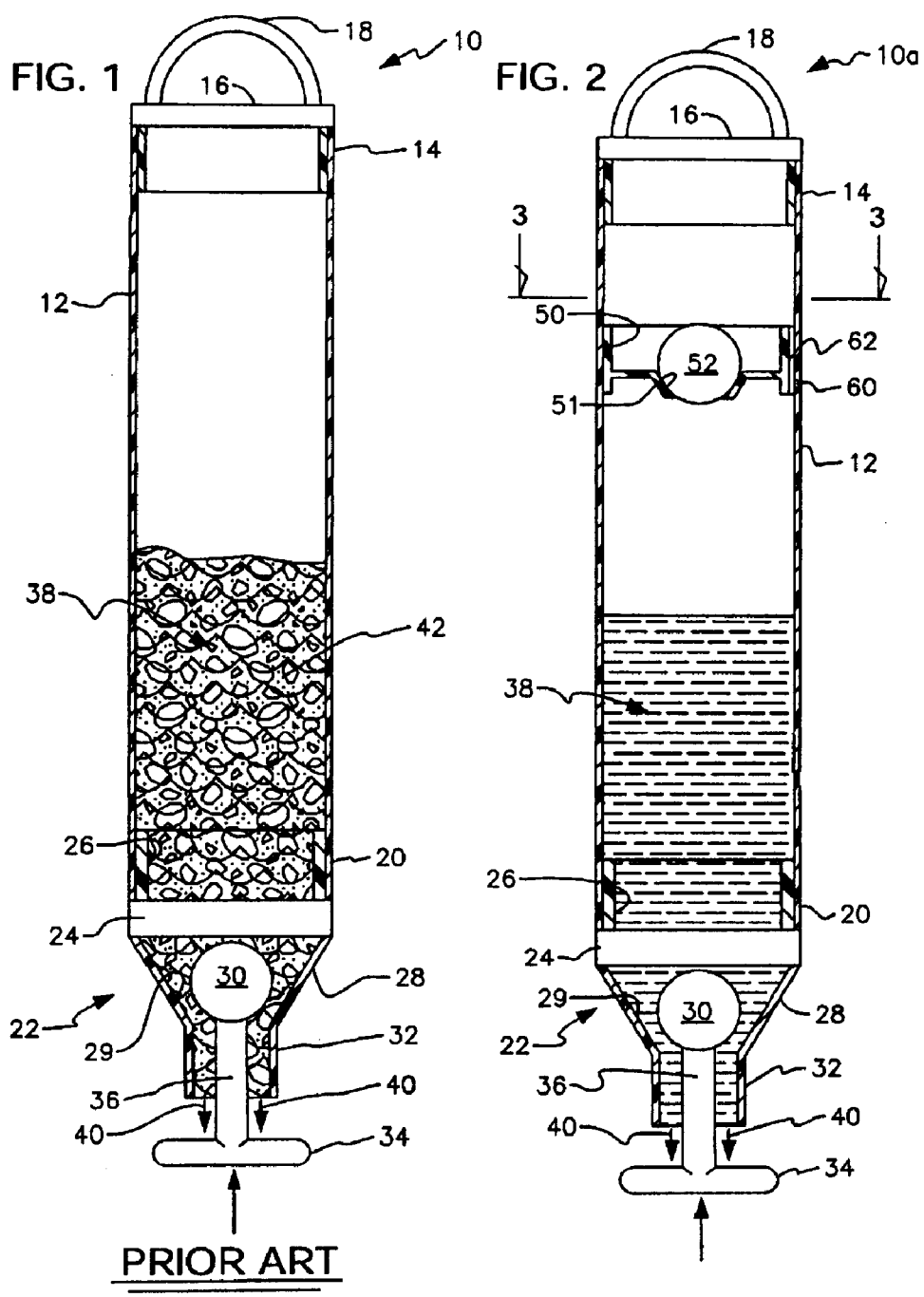

APPARATUS FOR INHIBITING CONTAMINATION OF SAMPLE DURING BAILER EMPTYING

BACKGROUND OF INVENTION

1. Field of the invention

This invention relates, generally, to bailers. More particularly, it relates to means and methods for inhibiting contamination by oxygen of a sample when emptying a bailer.

2. Description of the Prior Art

There are two commonly used methods for emptying a bailer.

In a first method, the bailer is maintained in an upright configuration in a substantially vertical plane, i.e., with the leading end or bottom of the bailer positioned directly below the trailing end or top thereof. A device known in the industry as a VOC device is positioned at the bottom of the bailer and manually lifted so that it lifts a check ball at the leading end of the bailer from its seat, thereby allowing the liquid fluid within the bailer to flow out. The liquid fluid exits the bailer and flows through an external filter to remove sand, mud, and the like. The filtered sample is collected into a container that is sent to a laboratory for analysis.

In a second method, the bailer is decanted from its open upper end, just as a glass of water may be emptied. The bailer is tilted from the vertical and gradually is inverted so that the entire sample flows therefrom. As in the VOC method, the decanted fluid is filtered and collected into a container.

Both methods have been used for many years but both have their shortcomings.

The first method is the more expensive method of the two, because it requires purchase of a VOC device for each sample taken. Since the sample contacts the VOC device as the sample flows from the bailer, the VOC device must be maintained in a sterile condition until used and it must be discarded or cleaned and recycled after each use to avoid cross contamination between samples. Moreover, since the user must hold the VOC device, there are times when the liquid fluid flowing from the bailer will contact the user's hands. This contaminates the sample and may injure the user if the sample is highly acidic or caustic.

Perhaps the most important shortcoming, however, is the contamination of the sample by oxygen in the atmosphere when the VOC device is used. When the VOC device lifts the check ball from its seat, air flows into the bailer from its leading, lower end and bubbles up to the surface of the sample at the top of the bailer. This flow of bubbles continues until the bailer has been emptied. The bubbles are large in size and number and introduce a considerable, easily visible turbulence into the sample as it flows from the bailer. Therefore, oxygen from the ambient atmosphere is mixed with the sample, thereby contaminating it.

The decanting method is less expensive since it requires no VOC device, and is safer because it is less likely to cause sample to contact a user's hand. However, the sample is also contaminated by contact with oxygen in the atmosphere as it is decanted. The amount of contamination is believed to be less than the contamination caused by the turbulent upward flow of bubbles introduced by use of a VOC device, but the contamination is still so significant that some environmental regulations call for the use of pumps to collect water from wells, to the exclusion of bailers.

Since pumps costs thousands of dollars per pump and bailers just a few dollars per bailer, the public is better served by the use of inexpensive bailers. Although a bailer cannot be reused, a pump must also be cleaned when it is moved from one well to another, and the cost of such cleaning far exceeds the cost of a bailer. The plastic from which a bailer is formed is also recyclable, further reducing the ultimate cost of a bailer.

What is needed, then, is a means for emptying a bailer that minimizes oxygen contamination as the bailer is emptied.

Environmental regulation agencies often require that liquid fluid be collected from a well or other body of water at a predetermined depth. However, known bailers have only one check valve, at the lower end thereof. Thus, when the bailer is raised from the body of liquid fluid, the liquid fluid in the bailer is free to flow out the top thereof, being replaced by liquid fluid near the surface of the body of water.

Thus there is a need for a bailer construction that can bring to the surface an amount of liquid fluid collected at a predetermined depth.

However, in view of the prior art considered as a whole at the time the present invention was made, it was not obvious to those of ordinary skill in the pertinent art how the identified needs could be fulfilled.

SUMMARY OF INVENTION

The long-standing but heretofore unfulfilled needs are now met by a new, useful, and nonobvious bailer that includes a cylindrical main body having a hollow interior adapted to hold a predetermined quantity of liquid fluid. A first check valve means is connected to a leading end of the bailer and a second check valve means is disposed in spaced relation to the first check valve means in the hollow interior near a trailing end of the bailer. A column of liquid fluid is captured within the hollow interior when the bailer is lowered into a body of liquid fluid. The column has a height equal to the spacing between the first and second check valve means. The column of liquid fluid is collected by inserting the bailer to a predetermined depth in the body of liquid fluid and retracting the bailer therefrom.

In a second embodiment, a vent opening is formed in the cylindrical main body at a preselected point between the first and second check valve means. The vent opening is preferably positioned in close proximity to the second check valve means on a leading side thereof. The vent opening enables the liquid fluid to flow from the hollow interior when the first check valve is unseated, in the absence of oxygen introduction from the leading end of the bailer.

In a third embodiment, a flat is formed in a cylindrical wall that forms a part of the second check valve means and a vent opening is formed in the cylindrical wall in radial juxtaposition to the flat. The vent opening substantially prevents oxygen contamination of the liquid fluid as the liquid fluid flows from the leading end of the bailer.

An important object is to provide a bailer that can collect samples of liquid fluid at a preselected depth.

Another important object of this invention is to provide a method for emptying a bailer that minimizes oxygen contamination of the sample.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which:

FIG. 1 is a side elevational view of a prior art bailer when being emptied by a VOC device;

FIG. 2 is a side elevational view of the novel bailer when being emptied by the novel method;

DETAILED DESCRIPTION

Figure 3:
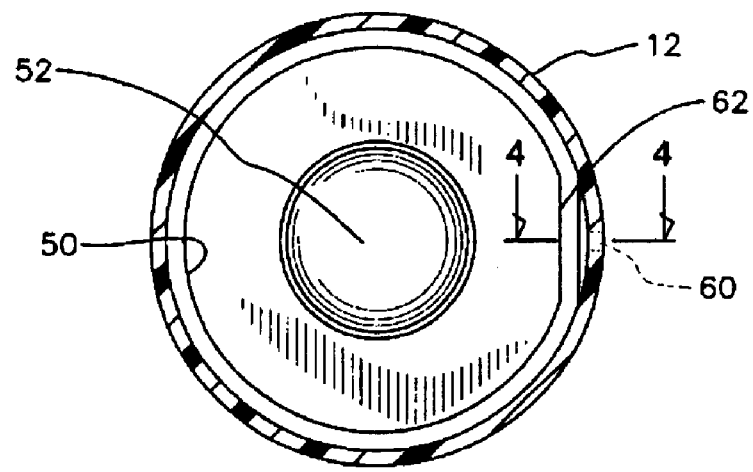
FIG. 3 is a sectional view taken along line 3—3 in FIG. 2.

Referring to FIG. 1, it will there be seen that the reference numeral 10 denotes a prior art bailer as a whole. The bailer is depicted in the process of being emptied of sample collected in a well or other body of liquid fluid.

Bailer 10 includes a cylindrical main body 12 having an upper or trailing end 14 closed by a closure means 16 having a handle 18 that is engaged by a rope or the like when the bailer is lowered into and lifted from a well or other body of liquid fluid, not shown. The lower or leading end of bailer 10 is denoted 20. A downspout, denoted 22 as a whole, includes base 24 from which projects annular wall 26 that slideably engages bailer lower end 20. A diameter-reducing frusto-conical wall 28 forms a valve seat 29 for check ball 30, and the straight part of the downspout is denoted 32.

Valve seat 29 and check ball 30 collectively form a first check valve means.

Bailer 10 is emptied by a diagrammatically-depicted VOC device having handle 34 and lift rod 36 that lifts check ball 30 from seat 29 so that liquid fluid 38 collected within the hollow interior of bailer 10 is able to flow therefrom as indicated by directional arrows 40. An external filter apparatus and collection container into which said liquid flows are not shown to simplify the drawing.

Large bubbles, collectively denoted 42, form at the leading end of bailer 10 when check ball 30 is lifted from seat 29, and flow to the top of the sample substantially in the manner depicted. Note that bubbles 42 are large and closely spaced to one another. Hundreds or thousands of them flow through the sample during the emptying procedure, creating a highly visible turbulence and mixing oxygen from the ambient atmosphere with sample 38.

FIG. 2 depicts the novel bailer apparatus in the process of being emptied. Note the absolute absence of bubbles such as bubbles 42 in the prior art bailer of FIG. 1.

In this particular embodiment, a novel second check valve means 50 is added to bailer 10a, near upper end 14 thereof. The valve seat is denoted 51 and check ball 52 is depicted seated in said valve seat.

Second check valve means 50 enables the bailer to capture sample liquid fluid in a well at a particular depth. Liquid fluid flows through the bailer from bottom to top as it is lowered into a body of liquid fluid to the desired depth. When the desired depth has been reached, the; bailer is retrieved and the upward motion of the bailer, together with the specific gravity of the check balls, causes both check balls to seat in their respective seats, thereby trapping liquid fluid between the two check valves.

For example, suppose an environmental regulation agency has requested that a sample of liquid fluid be taken from a well at a depth between twelve (12) and fourteen (14) feet. Second check valve means 50 is positioned a distance of two (2) feet from the first check valve means and the bailer is lowered into the body of liquid fluid until the first check valve means has reached has reached a depth of fourteen (14) feet, as indicated by markings on the rope or other lowering means, not shown. The bailer is then retrieved.

If a VOC device is employed to empty the bailer after it has returned to the surface with its sample of liquid fluid, the liquid fluid collected at said depth of twelve to fourteen feet will become contaminated with oxygen as in the prior art bailer of FIG. 1.

This invention includes a novel means that enables bailer 10a to be emptied without decanting it from the top and without introducing bubbles.

Vent opening 60 (FIGS. 2–4) may be formed in cylindrical main body 12 at any point level with or below second check valve means 50 and above check valve seat 29 of the first check valve means. However, since hydrostatic pressure increases with depth, leakage through vent opening 60 increases with distance from check valve means 50. Accordingly, little leakage occurs if vent opening 60 is spaced level with or only slightly below second check valve means 50.

Figure 4:
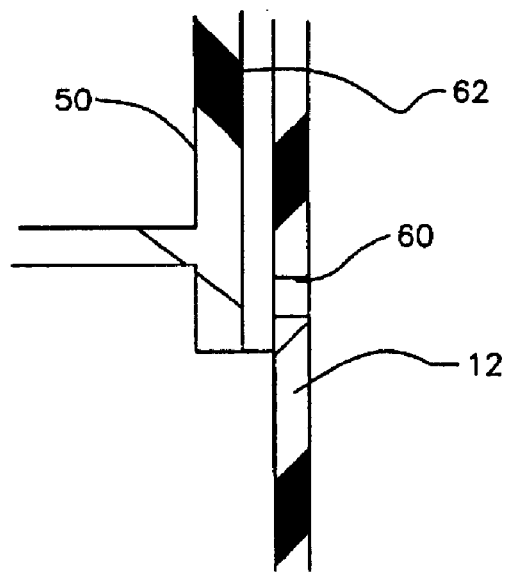
FIG. 4 is a sectional view taken along line 4—4 in FIG. 3.

The preferred location of vent opening 60 is depicted in FIGS. 2–4. A small flat 62 is formed in second check valve means 50, and vent opening 60 is formed in main body 12 at any location that is radially outward of said flat. In this way, vent opening 60 is above the level of collected liquid fluid trapped between the first and second check valve means and no leakage occurs therethrough.

When bailer 10a is manufactured, flat 62 could be eliminated and vent opening 60 could be formed in sidewall 12 downwardly of check valve means 50. However, unwanted leakage though said vent opening would then result. If such a vent opening is provided, it may be advantageously circumscribed by an annular scoring line about its periphery to facilitate punching out the opening by a user in the field. A flat, not shown, could be formed in the cylindrical wall of the bailer main body in surrounding relation to such vent opening to facilitate the punching procedure.

In the alternative, bailer 10a may be manufactured with vent opening 60 pre-formed therein at a preselected location downwardly of second check valve moans 50. In that case, a closure means, not shown, could be secured to cylindrical main body 12 by a living hinge and positioned in closing relation to the opening. The user would then merely need to pull the closure means from vent opening 60. Moreover, the closure means could be provided as a separate piece unconnected to bailer 10a.

U.S. Pat. No. 5,996,800, awarded to the present inventor on Dec. 7, 1999, entitled Resealable Plastic Bag Having Venting Means, which disclosure is hereby incorporated by reference, discloses a suitable closure means that could be employed to close vent opening 60 if it is formed in main body 12 at a preselected point below its depicted position.

FIG. 2 demonstrates the value of vent opening 60. In that figure, liquid fluid 38 is flowing from the leading end of bailer 10a because VOC device 34 has lifted check ball 30 from valve seat 29. The bailer is about half empty at the moment in time depicted in FIG. 2, and no bubbles have appeared in sample 38. Nor will any bubbles appear at anytime during the emptying procedure. Vent opening 60 admits air into the hollow interior of bailer 10a so that air need not enter, thereinto from the lower end of the bailer as in the prior art method depicted in FIG 1. This eliminates bubbles 42 of FIG. 1, the turbulence caused thereby, and the concomitant oxygen contamination.

Vent opening 60 is preferably positioned level wit or just below second check valve means 50 but it will prevent oxygen contamination of the sample as long as it is positioned anywhere between second check valve means 50 and first check valve seat 29. However, since the hydrostatic pressure on cylindrical sidewalls 12 of bailer 10a increases wit depth of liquid fluid 38, greater leakage will occur as the vent opening is spaced further from second check valve means 50 as aforesaid.

The novel bailer thus enables collection of sample at a specified depth and enables delivery of that sample to a lab in the substantial absence of oxygen contamination. It thus matches or exceeds the capabilities of a pump-based sample collection apparatus, and does so at a tiny fraction of the cost.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,
What is claimed is:

1. A bailer, comprising:
   a cylindrical main body having a hollow interior adapted to hold a quantity of liquid fluid;
   a first check valve means connected to a leading end of said bailer;
   a second check valve means disposed in spaced relation to said first check valve means;
   said second check valve means positioned in said hallow interior near a trailing end of said bailer;
   a vent opening formed in said cylindrical main body at a point between said first and second check valve means;
   whereby a column of liquid fluid is contained within said hollow interior when said bailer is lowered into a body of liquid fluid, said column having a height equal to the spacing between said first and second check valve means;
   whereby said column of liquid fluid is collected by inserting said bailer to a predetermined depth in said body of liquid fluid and retracting said bailer from said body of liquid fluid.

2. The bailer of claim 1, wherein said vent opening is positioned in close proximity to said second check valve means on a leading side thereof.

3. A bailer, comprising:
   a cylindrical main body having a hollow interior adapted to hold a quantity of liquid fluid;
   a first check valve means connected to a leading end of said bailer;
   a second check valve means disposed in spaced relation to said first check valve means;
   said second check valve means positioned in said hollow interior near a tailing end of said bailer;
   said hollow interior adapted to bold a column of liquid fluid, said column having a height equal to the spacing between said first and second check valve means;
   a vent opening formed in said cylindrical main body at a point between said first and second check valve means;
   whereby said column of liquid fluid is collected by inserting said bailer to a predetermined dept and by retracting said bailer; and
   whereby said vent opening enables said liquid fluid to flow from said hollow interior when said first check valve is unseated.

4. The bailer of claim 3, wherein said vent opening is positioned in close proximity to said second check valve means on a leading side thereof.

5. A bailer, comprising:
   a cylindrical main body having a hollow interior adapted to bold a quantity of liquid fluid;
   a first check valve means connected to a leading end of said bailer;
   a second check valve means positioned in said hollow interior in trailing relation to said first check valve means;
   said second check valve means including a valve seat;
   said valve seat including a cylindrical wall that is press fit into said hollow interior of said cylindrical main body to maintain said second check valve means in position;
   a flat formed in said cylindrical wall of said valve seat;
   a vent opening formed in said cylindrical main body of said bailer in radially spaced relation to said flat;
   a column of liquid fluid being captured within said hollow interior between said first and second check valve means when said bailer is lowered into a body of liquid fluid and retrieved therefrom;
   said bailer being emptied by opening said first check valve means to allow liquid fluid to drain from said leading end of said bailer;
   said vent opening substantially preventing oxygen contamination of said liquid fluid as said liquid fluid flows from said leading end of said bailer.

* * * * *